United States Patent [19]
Johnson et al.

[11] Patent Number: 5,436,325
[45] Date of Patent: Jul. 25, 1995

[54] METHOD FOR MAKING 2-FLUORO-2-DEOXYGLUCOSE

[75] Inventors: Bruce F. Johnson, Scotia, N.Y.; Maxim Y. Kiselev, Waukesha, Wis.; Johan Ulin, Uppsala, Sweden

[73] Assignee: General Electric Company, Schenectady, N.Y.

[21] Appl. No.: 276,725

[22] Filed: Jul. 18, 1994

Related U.S. Application Data

[63] Continuation of Ser. No. 35,421, Mar. 22, 1993, abandoned.

[51] Int. Cl.⁶ .............................................. C07H 1/00
[52] U.S. Cl. ................................. 536/4.1; 536/18.4; 536/18.5
[58] Field of Search .................. 536/18.4, 18.5, 4.1; 424/1.1

[56] References Cited

FOREIGN PATENT DOCUMENTS 0167103  6/1985  Germany ............................ 424/1.1

OTHER PUBLICATIONS

Article-2-Deoxy-2-[18F]Fluoro-D-Glucose for Metabolic Studies: Current Status, JS Fowler and AP Wolf, Appl. Radiat. Isot. vol. 37, No. 8, pp. 663-668 (1986).
Article-Recommendation for A Pratical Production of [2-18F]Fluoro-2-Deoxy-D-Glucose, H. Coenen et al, Appl. Radiat. Isot. vol. 38, No. 8, pp. 605-610 (1987).
Article-Efficient Stereospecific Synthesis of No-Carrier-Added 2-[18F]-Fluoro-2-Deoxy-D-Glucose Using Aminopolyether Supported Nucleophilic Substitution, K. Hamacher et al, J. Nucl. Med. 27, 235 (86), p. 235238.
Article-Computer-aided Synthesis (CAS) of No-carrier-added 2-[18F]Fluoro-2-Deoxy-D-Glucose: An Efficient Automated System for the Aminopolyether-supported Nucleophilic Fluorination, K. Hamach et al, Appl. Radiat. Isot. vol. 41, No. 1 pp. 49-55 (1990).
Article-Robotic Production of 2-Deoxy-2-[18F]-Fluoro-D-Glucose: A Routine Method of Synthesis Using Tetrabutylammonium [18F]Fluoride, J. W. Brodack et al. Appl. Raiiiat. Iost. vol. 39, No. 7, pp. 699-703 (1988).
Article-Routine Production of 2-Deoxy-2-[18F]-Fluoro-D-Glucose by Direct Nucleophilic Exchange on a Quaternary 4-Aminopyridinium Resin, SA Toorongian et al., Nucl. Med. Biol. vol. 17, No. 3, pp. 273-279 (1990).

*Primary Examiner*—Douglas W. Robinson
*Assistant Examiner*—James O. Wilson
*Attorney, Agent, or Firm*—William H. Pittman

[57] ABSTRACT

A method is provided for preparing [$^{18}$F]2-fluoro-2-deoxyglucose with an anion exchange resin by effecting an exchange reaction between an aqueous solution of [$^{18}$F]fluoride containing an alkali metal carbonate or bicarbonate, such as sodium bicarbonate, and an anion, such as bicarbonate or carbonate, on the anion exchange resin followed by the displacement reaction with 1,3,4,6-tetra-O-acetyl-2-O-trifluoromethanesulfonyl-β-D-mannopyranose to form the resulting 2-fluoro-2-deoxyglucose tetraacetate. Improved yields of the [$^{18}$F]2-fluoro-2-deoxyglucose are obtained when the alkali bicarbonate or carbonate is used in the target water.

4 Claims, No Drawings

METHOD FOR MAKING 2-FLUORO-2-DEOXYGLUCOSE

CROSS-REFERENCE TO RELATED APPLICATION

This application is a continuation of application Ser. No. 08/035,421, filed Mar. 22, 1993, now abandoned.

BACKGROUND OF THE INVENTION

The present invention relates to a method for making 2-fluoro-2-deoxy-D-glucose or [$^{18}$F]2FDG, utilizing an anion exchange resin. More particularly, the present invention relates to the use of an anion exchange resin to more effectively trap [$^{18}$F]fluoride ion, involving the treatment of the anion exchange resin having an anion, such as a carbonate or bicarbonate anion, with an aqueous solution of [$^{18}$F]fluoride ion target water and an alkali metal carbonate or bicarbonate salt, such as sodium bicarbonate.

Prior to the present invention, various procedures were used for making [$^{18}$F]2FDG, which is used as a radiopharmaceutical for Positron Emission Tomography (PET). Considerable effort has been expended in the development and refinement of such procedures. Because [$^{18}$F]fluoride ion has a low decay energy, (0.64 MEV), it allows the highest inherent resolution during PET measurements and has a relatively convenient half life of 109.7 min. The following equation illustrates the preferred procedure for making [$^{18}$F]2FDG starting with a solution of 1,3,4,6-tetra-O-acetyl-2-O-trifluoromethanesulfonyl-β-D-mannopyranose or "triflate":

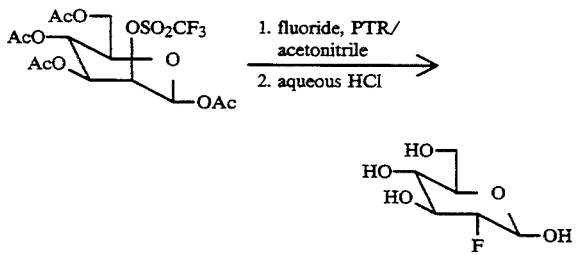

where Ac is acetate, and "PTR" means phase-transfer reagent.

One method of synthesizing [$^{18}$F]2FDG by the above procedure is shown by Hamacher et al., Journal of Nuclear Medicine, 27:235-238, (1986). Hamacher et al. employ an aminopolyether [Kryptofix 222 or K222]-potassium carbonate complex as a phase-transfer catalyst for [$^{18}$F]fluoride. An additional procedure for making [$^{18}$F]2FDG is shown by Brodack et al., Applied Radiation and Isotope, Volume 39, No. 7, pages 699-703 (1988) involving the employment of a tetrabutylammonium hydroxide as a phase-transfer catalyst in place of the aminopolyether potassium complex of Hamacher et al. Although Brodack et al. disclose that the triflate reacts with [$^{18}$F]fluoride ion using the tetrabutylammonium counter ion, a yield of 12-17% is reported which is significantly below the level considered acceptable for commercial robotic production of [$^{18}$F]2FDG.

The above procedures utilizing a phase-transfer reagent for [$^{18}$F]2FDG synthesis have an inherent disadvantage particularly if Kryptofix 222 is used as the phase-transfer catalyst. Kryptofix is toxic and minor traces of the phase-transfer catalyst are often difficult to remove from the final patient dose. Elaborate methods have to be used therefore to eliminate any traces of the phase-transfer catalyst before it is used. The application of automation using such PTR is therefore rendered more difficult.

An improvement in the use of a phase-transfer catalyst for making [$^{18}$F]2FDG is shown by Johnson et al., U.S. Pat. No. 5,169,942, which utilizes a less toxic PTR, such as a tetraalkylammonium bicarbonate. However, it has been found desirable to minimize any traces of the PTR from the final dose before intravenous use which complicates the implementation of this procedure.

As shown by S. A. Toorongian et al., cited below, alternative methods for making [$^{18}$F]2FDG are also known which utilize an anion exchange resin to trap the [$^{18}$F]fluoride ion. However, the yields of [$^{18}$F]2FDG made by the anion exchange resin procedure have been found to be significantly less than methods employing a PTR. It would be desirable therefore to provide a procedure for improving the yield of [$^{18}$F]2FDG by using an anion exchange resin to more effectively trap the [$^{18}$F]fluoride ion and improve the yields of [$^{18}$F]2FDG.

SUMMARY OF THE INVENTION

The present invention is based on the discovery than improved yields of [$^{18}$F]2FDG can be obtained with an anion exchange resin having a carbonate or bicarbonate anion. It has been found that if prior to direct contact between the [$^{18}$F]fluoride ion containing target water and the anion exchange resin, the [$^{18}$F]fluoride ion target water is mixed with an alkali metal carbonate or bicarbonate salt in proportions as set forth below, an enhancement in [$^{18}$F]2FDG yields can be obtained.

STATEMENT OF THE INVENTION

There is provided by the present invention, a method for making [$^{18}$F]2-fluoro-2-deoxy-D-glucose comprising, comprising a silanol-free organosilicon resin powder made in accordance with claim 1, a vinyl substituted methylpolysiloxane fluid, a silicon hydride siloxane fluid, an inhibitor and an effective amount of a platinum catalyst.(2) effecting the displacement of the [$^{18}$F]fluoride ion on the anion exchange resin of (1) with the trifluoromethanesulfonyl ester leaving group of an organic solvent solution of 1,3,4,6-tetra-O-acetyl-2-O-trifluoromethanesulfonyl-β-D-mannopyranose, (3) treating with an aqueous hydrogen halide solution, the residue of the effluent of (2), after it has been collected from the anion exchange resin and stripped of organic solvent to effect the hydrolysis of the resulting tetraacetyl 2-fluoro-2-deoxyglucose, and (4) recovering the resulting [$^{18}$F]2-fluoro-2-deoxyglucose from (3).

Among the ion exchange resins which can be employed are for example, polystyrene resin functionalized with piperidinopyridinium groups which serve to trap the [$^{18}$F]fluoride ion and act as a phase-transfer reagent without contaminating the mixture which is injected into the patient. The preferred anion exchange resin is the "Mulholland" anion exchange resin which preferably has a displaceable carbonate or bicarbonate anion ionically bound to the pyridinium group.

During the initial exchange reaction between the anion exchange resin and the [$^{18}$F]fluoride ion, the [$^{18}$F]fluoride ion is introduced as an aqueous solution with an alkali metal carbonate or bicarbonate salt. Although sodium bicarbonate is preferred other alkali metal bicarbonates or carbonates can be used, such as potassium bicarbonate and sodium carbonate. The [$^{18}$F]fluoride ion is preferably added to an aqueous solution of the alkali metal bicarbonate within the aforedescribed concentration ranges as set forth in the Statement of The Invention.

After passage of the aqueous solution of [$^{18}$F]fluoride ion and alkali metal bicarbonate or carbonate through the anion exchange resin to effect exchange and more effectively trap the [$^{18}$F]fluoride ion on the anion exchange resin, the anionic exchange resin can be treated with an anhydrous organic solvent such as acetonitrile to remove water. The anionic exchange resin can then be heated from 70° C. to 90° C. prior to passage of an organic solvent solution of the "triflate", 3,4,6-tetra-O-acetyl-2-O-trifluoromethanesulfonyl-β-D-mannopyranose to effect exchange between the triflate leaving group and the [$^{18}$F]fluoride ion. The anionic exchange resin can then be rinsed with additional organic solvent.

The effluent from the anionic exchange resin can be stripped of organic solvent under a stream of nitrogen or helium under reduced pressure. The residue can then be treated with an aqueous acid halide, such as an 2N HCl solution and refluxed for a sufficient period of time, such as 10 to 20 minutes to effect the hydrolysis of the [$^{18}$F]2FDG tetraacetate. The resulting solution can then be passed through ion retardation resin, reverse phase silica gel and an alumina sep-pak into a collection vial. Radioactivity in the collection vial can be measured and the purity assessed by TLC.

In order that those skilled in the art will be better able to practice the present invention, the following example is given by way of illustration and not by way of limitation. All parts are by weight.

EXAMPLE

There was added 0.5 to 1.5 μmol of sodium bicarbonate and 10 to 500 μl of deionized water to 1.0 to 1.5 ml of water which was obtained from a cyclotron target containing 0.5 to 10 mCi of [$^{18}$F]fluoride in a receiver vessel. The resulting solution was passed through a column having 10–20 mg of a 2% crosslinked anion exchange resin, specifically (Mulholland) anion exchange resin in the carbonate form, (shown by S. A. Toorongian et al; NuCl.Med. Biol. 17:273–279 (1990)Int. J. Radiat. Appl. Instrum. Part B) . One ml of dry acetonitrile was then passed through the resin to remove water. The anion exchange resin was then heated to 80° to 90° C. and a solution of 1,3,4,6-tetra-O-acetyl-2-O-trifluoromethanesulfonyl-β-D-mannopyranose (triflate) in acetonitrile where the solution contained 30 mg of the (triflate) in 0.75 ml of acetonitrile, was pushed through the resin column to effect displacement. The column was then rinsed with 0.5 ml of acetonitrile. Effluent was collected in a plastic vessel and the acetonitrile was removed in a stream of nitrogen with heating under reduced pressure. The resulting residue was then treated with 2 ml of 2N hydrochloric acid and refluxed for 15 minutes to effect hydrolysis of the [$^{18}$F]2FDG tetraacetate. The resulting solution was passed through an ion retardation resin (Biorad AG-11AS), reverse phase C18 silica gel (Supelco SPE), (Waters) and alumina sep pak (Waters) to a collection vial. The radioactivity in the collection vial was measured and the purity assessed by TLC. The following results were obtained where the reported yields are not decay corrected, and n is the number of runs:

TABLE 1

| Yields of [$^{18}$F]2FDG | | | |
|---|---|---|---|
| 0.5 μmol NaHCO$_3$ in Target Water | Yield | 95% confidence level | n |
| Yes | 39.5% | 4.4% | 7 |
| No | 35.7% | 2.3% | 21 |

The above procedure was repeated except that the yield of the [$^{18}$F]2FDG netraacetate was measured. There was used 0.3 μmol of sodium bicarbonate solution in the target water and the column was heated at 80° C. to 90° C. The following results were obtained where the yields are corrected for decay:

TABLE 2

| Yields of [$^{18}$F]2FDG Tetraacetate | | | | |
|---|---|---|---|---|
| 0.3 μmol NaHCO$_3$ In Target Water | Column Temp (°) | Yield | 95% confidence level | n |
| Yes | 90° C. | 69.6% | 4.7% | 12 |
| No | 90° C. | 56.0% | 11.7% | 4 |
| Yes | 80° C. | 69.4/% | 2.5% | 5 |
| No | 80° C. | 53.3% | 9.0% | 6 |

As shown by the results in Tables 1 and 2, significantly improved yields of [$^{18}$F]2FDG and the corresponding tetraacetate were obtained when NaHCO$_3$ was used in the target water in accordance with the practice of the present invention.

Although the above example is directed to only a few of the very many variables which can be used in the practice of the method of the present invention, it should be understood that the present invention is directed to the use of a much broader variety of alkali metal carbonates or bicarbonates as well as conditions shown in the description preceding this example.

What is claimed is:

1. A method for making [$^{18}$F]2-fluoro-2-deoxy-D-glucose comprising,
    1) effecting an anion exchange reaction between [$^{18}$F]fluoride ion and an anion ionically bound to an anionic exchange resin, where the anionic exchange reaction between the [$^{18}$F]fluoride ion and the ionically bound anion on the anionic exchange resin is facilitated by using the [$^{18}$F]fluoride ion in the form of an aqueous solution of [$^{18}$F]fluoride ion and 10 to 60 nmol of an alkali metal bicarbonate salt, per μmol of anionic sites on the anionic exchange resin,
    2) heating the anion exchange resin to 70° C. to 90° C. and effecting the displacement of the [$^{18}$F]fluoride ion on the anion exchange resin of (1) with the trifluoromethanesulfonyl ester leaving group of an organic solvent solution of 1,3,4,6-tetra-O-acetyl-2-O-trifluoromethanesulfonyl-β-D-mannopyranose,
    3) treating with an aqueous hydrogen halide solution, the residue of the effluent of (2), after it has been collected from the anion exchange resin and stripped of organic solvent to effect the hydrolysis of the resulting tetraacetyl 2-fluoro-2-deoxyglucose, and
    4) recovering the resulting [$^{18}$F]2-fluoro-2-deoxyglucose from (3).

2. A method in accordance with claim 1, where the anion exchange resin is a polystyrene resin functionalized with piperidinopyridinium groups.

3. A method in accordance with claim 1, where the alkali metal bicarbonate used in combination with [$^{18}$F]fluoride ion is sodium bicarbonate.

4. A method in accordance with claim 1, where the organic solvent is acetonitrile.

* * * * *